United States Patent [19]

Winner

[11] Patent Number: Plant 6,652

[45] Date of Patent: Mar. 7, 1989

[54] VARIETY OF GERANIUM NAMED 67

[75] Inventor: Blair L. Winner, Lompoc, Calif.

[73] Assignee: 501 Denholm Seeds, Lompoc, Calif.

[21] Appl. No.: 73,809

[22] Filed: Jul. 15, 1987

[51] Int. Cl.[4] ..... A01H 5/00
[52] U.S. Cl. ..... Plt./68
[58] Field of Search ..... Plt./68

*Primary Examiner*—Robert E. Bagwill

*Attorney, Agent, or Firm*—Webb, Burden, Ziesenheim & Webb

[57] ABSTRACT

A new geranium cultivar is distinguished by its compact plant, early flowering and delicate color balance from margin to center with an overall pastel pink appearance. The plant is strong, vigorous and stable and withstands heat. Flowers are retained while vegetation continues to grow.

1 Drawing Sheet

The present invention comprises a new and distinct cultivar of *Pelargonium hortorum* which is a zonal geranium known by the varietal name Capri. The new varietey Capri (Oglevee No. 67, Denholm No. 5525) was discovered in a selective breeding program by Mr. Blair L. Winner. The new cultivar was derived from the selfing of the variety "Glacier Claret" (patent pending).

The principal difference between the new cultivar and "Glacier Claret" is one of flower color. The new cultivar is a salmon color whereas "Glacier Claret" has a red-purple flower color.

The new cultivar was discovered in January of 1983 at Denholm Seeds in Lompoc, Calif., was first asexually reproduced by cuttings by Denholm Seeds at Lompoc, Calif. and has been repeatedly asexually reproduced by cuttings at Oglevee Associates, Inc. in Connellsville, Pa. over a 36 month period. It has been trial and field tested at Connellsville, Pa. yearly since the spring of 1984. It has been found to retain its distinctive characteristics through successive propagations.

The new cultivar when grown in a greenhouse in Connellsville, Pa. using full natural light, 60° F. night temperature, 68° F. day temperature and 71° F. vent temperature and grown in a soilless media and constant fertilizer of 275–300 parts per million nitrogen and potassium, has a response time from a rooted cutting to a flowering plant of six weeks.

DESCRIPTION OF THE DRAWING

The accompanying drawing illustrates the new cultivar, the color being as true as possible with color illustrations of this type.

DESCRIPTION OF THE NEW PLANT

The following detailed description sets forth the characteristics of the cultivar. The data which define these characteristics were collected from asexual reproductions carried out by Oglevee Associates, Inc. in Connellsville, Pa. The plant histories were taken on plants blossomed under natural light in a greenhouse and color readings were taken indoors under 200–220 foot candles of fluorescent cool white light. Color references are primarily to the R.H.S. Colour Chart of The Royal Horticultural Society of London.

THE PLANT

Classification:
- *Botanical.*—*Pelargonium* × *hortorum.*
- *Commercial.*—Zonal geranium.

Form: Semi-dwarf; free basal branching; compact growth; flowers close to foliage; free and early flowering.

Height: 24.0–30.0 cm from media surface.

Growth: Free branching from base; short internodes.

Strength: Stands upright without artificial support.

Foliage: Stalked leaf attachment; faint leaf zoning.

Leaves:
- *Size.*—5.5–8.5 cm across. Shape: Reinform; cordate base.
- *Margin.*—Crenate.
- *Texture.*—Pubescent: Dull (Non-reflective).
- *Color.*—Top: Margin Green group 137C; center green group 138B.
- *Bottom.*—Green group 138C.
- *Ribs and veins.*—Palmate veination; yellow-green group 145C.

Petioles: 5.0–7.0 cm in length; yellow-green group 144A.

Stem:
- *Color.*—Green group 137C and yellow-green group 144B.
- *Internodes.*—1.4 cm in length.

The buds:
- *Shape.*—Upright, hemispherical cluster.

Size: 3.0–4.0 cm across.

INFLORESCENCE

Blooming habit: Continuous; upright; semi-double; slowly shatters; hemi-spherical in shape.

Size: 9.0–11.0 cm across.

Borne: Umbel; florets on pedicel; pedicel on peduncle; 2.0–4.0 cm above florage.

Florets:
- *Form.*—Flat to slightly cupped; with petaloids; ovate.
- *Color.*—Front (margin), red group 49D, (center) red group 38A.
- *Back.*—Red group 49D.
- *Petals.*—5–7 in number; separate—not united; margin entire, obovate; palmate veination; smooth; flat to slightly cupped.
- *Size.*—4.0–5.0 cm across.

*Texture and appearance.*—Smooth surface; reflective.

Petaloids:

*Quantity.*—3–5 in number.

*Shape.*—narrow; elongated; twisted.

*Color.*—Front; Red group 38A.

*Back.*—Red group 49D.

Pedicel:

*Length.*—2.0–3.0 cm.

*Color.*—Yellow-green group 145A.

Peduncle: Arises from node; opposite leaf petiole; 8.0–16.0 cm in length; yellow-green group 144A.

REPRODUCTIVE ORGANS

Stamens:

*Anthers.*—Resembles the color of the center of floret; 1.0–2.0 mm in length.

*Filaments.*—White at base; coloring toward tip same as center of floret; irregular in shape; same petaloid; flat at base and twisted at tip; 5.6 mm in length.

*Pollen.*—Golden brown initially and later turning dark brown.

Pistils:

*Number.*—1 with 5 parted stigma.

*Length.*—0.8–0.9 cm in length.

*Stigma.*—5; parted, color same as center of floret.

*Style.*—1; pale red to reddish color; 2.0–3.0 mm in length.

Ovaries: 3.0–5.0 mm in length; yellow-green; very pubescent (0.1–0.5 mm long); superior.

Fruit: None observed.

The new cultivar is characterized by a compact plant, early flowering, strong, vigorous and stable plant, withstands heat and retains flower while continuing to provide vegetation, delicate color balance from margin to center with overall pastel pink appearance.

I claim:

1. A new and distinct variety of geranium plant substantially as shown herein and described and parts thereof.

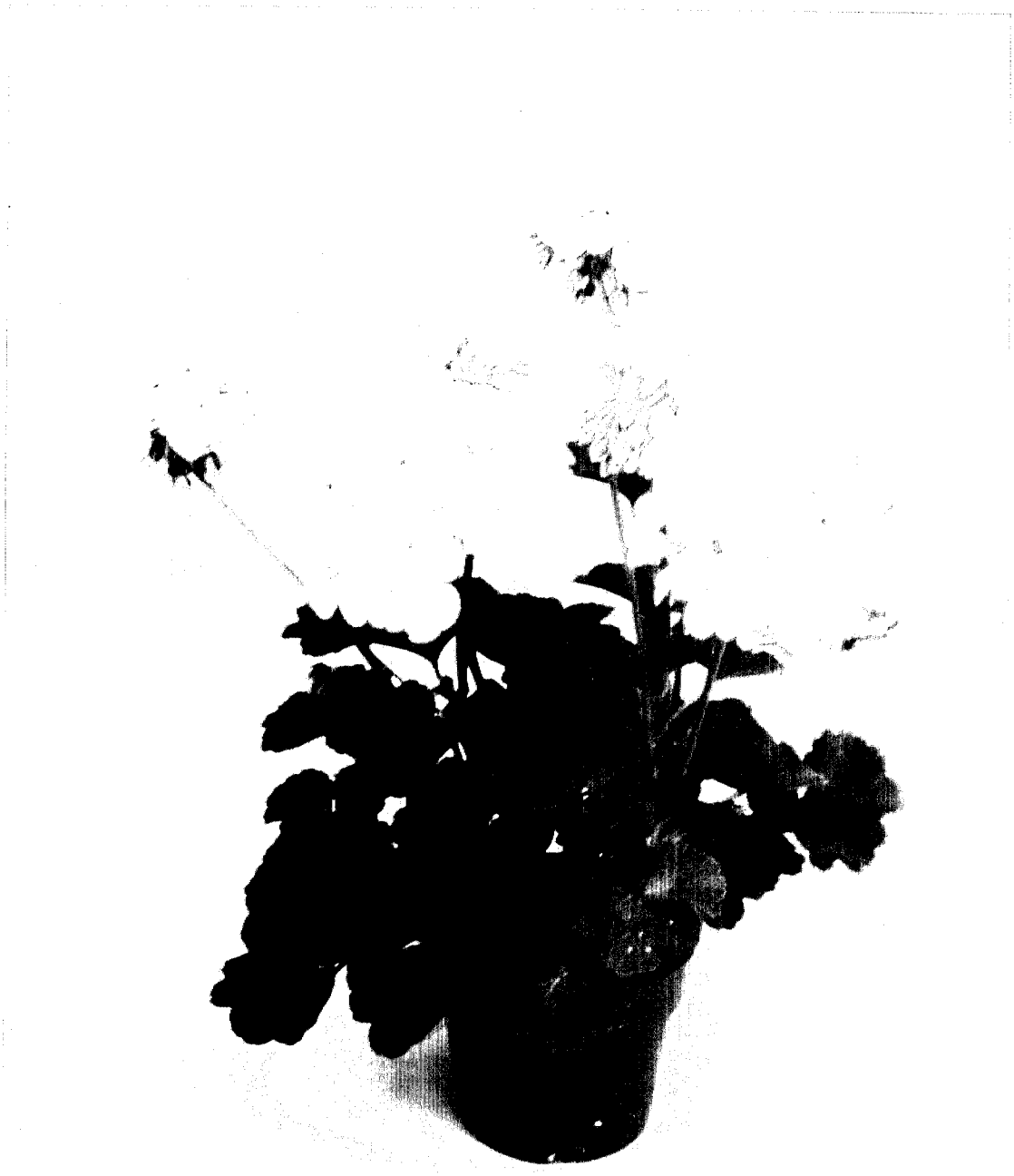

* * * * *